United States Patent [19]

Brandhorst et al.

[11] Patent Number: 5,181,918
[45] Date of Patent: Jan. 26, 1993

[54] GRANULES SYRINGE

[75] Inventors: Gerd Brandhorst, Muenchen; Wolfgang Taeschner, Schondorf, both of Fed. Rep. of Germany

[73] Assignee: THERA Patent GmbH & Co. KG Gesellschaft Fuer industrielle Schutzrechte, Seefeld, Fed. Rep. of Germany

[21] Appl. No.: 739,503

[22] Filed: Aug. 2, 1991

[30] Foreign Application Priority Data

Aug. 10, 1990 [DE] Fed. Rep. of Germany ............. 9011685[U]

[51] Int. Cl.$^5$ ............................................. A61F 7/00
[52] U.S. Cl. ...................................... 606/92; 604/187
[58] Field of Search ........................... 604/56-60, 604/218, 197, 198, 222, 236, 237; 606/92-95

[56] References Cited

U.S. PATENT DOCUMENTS

| | | | |
|---|---|---|---|
| 405,100 | 6/1889 | Kloppe | 604/197 |
| 4,405,249 | 9/1983 | Scales | 606/93 |
| 4,551,135 | 11/1985 | Gorman et al. | 623/16 |
| 4,625,722 | 12/1986 | Murray | 606/94 |
| 4,632,672 | 12/1986 | Kvitrud | 604/222 |
| 4,653,487 | 5/1987 | Maale | 606/94 |
| 4,751,921 | 6/1988 | Park | 606/93 |
| 4,769,011 | 9/1988 | Swaniger | 604/218 |
| 4,820,306 | 4/1989 | Gorman et al. | 623/16 |

FOREIGN PATENT DOCUMENTS

| | | | |
|---|---|---|---|
| 2519330 | 3/1976 | Fed. Rep. of Germany | 604/222 |
| 2814353 | 10/1978 | Fed. Rep. of Germany | 606/93 |
| 3701190 A1 | 7/1988 | Fed. Rep. of Germany | . |

OTHER PUBLICATIONS

Exeter Pressurizer System, Howmedica, Inc., Orthopaedics Division 1979.
"Hydroxlapatite Non-resorbable, Affordable, in a New, Improved Syringe". Leaflet by Orthomatrix.

*Primary Examiner*—C. Fred Rosenbaum
*Assistant Examiner*—Manuel Mendez
*Attorney, Agent, or Firm*—Foley & Lardner

[57] ABSTRACT

A granules syringe, particularly for impregnating granules of a bone cement with blood and for dispensing the impregnated granules, includes a transparent tubular barrel for receiving the granules between a porous front cover and a porous plug. A piston which is separate from the plug and has an integrated seal is disposed behind the plug. When the piston is retracted, the seal is closed so that the vacuum is generated to suck the blood through the porous cover into the granules. When the piston is subsequently advanced, the seal opens so that air has been removed from the granules and passed through the porous plug is permitted to escape rewardly. Upon removal of the cover, the plug is then advanced by the piston to dispense the impregnated granules.

5 Claims, 1 Drawing Sheet

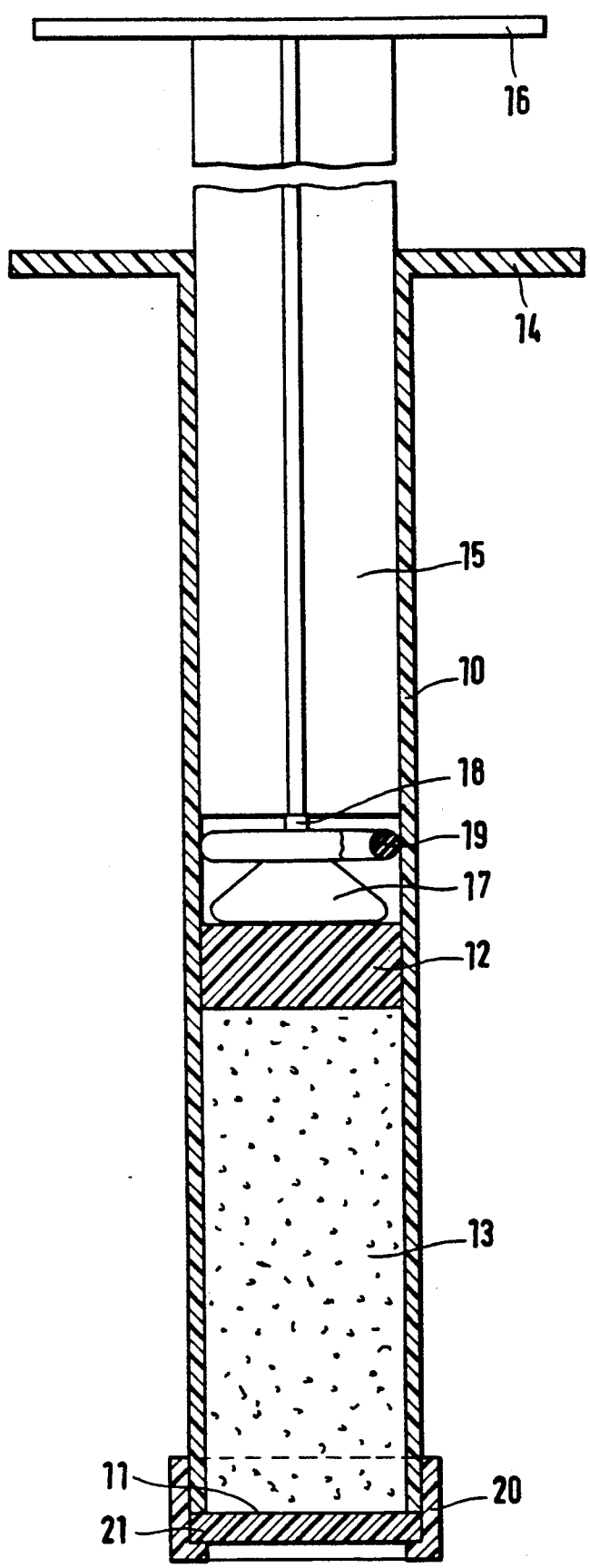

GRANULES SYRINGE

BACKGROUND OF THE INVENTION

In surgery, there are occasions when cavities formed in a bone are filled by a mass consisting of granules of bone cement impregnated with the patient's own blood. For this filling step, a granules syringe is commercially available from Orthomatrix, Inc., which includes a transparent barrel for receiving the granules between a front cap and a piston reciprocally disposed within the barrel. The cap is provided with a screen to allow the impregnating liquid to pass while retaining the granules. A piston rod extending beyond the open rear end of the barrel permits the piston to be manually retracted and advanced.

In use, the syringe is immersed with its front cap into blood taken from the patient, and the blood is drawn in by retracting the piston. By shaking the device, the granules are subsequently mixed with the blood. For an efficient mixing, the volume of the chamber must be greater than the total volume occupied by the granules and the blood. In other words, by retracting the piston air must be taken in, in addition to blood. When the mixing step has been completed, this air must be expelled by advancing the piston, before the mixture of bone cement and blood may be applied to the bone cavity by further advancement of the piston.

A problem with the known granules syringe resides in the fact that a thorough impregnation of the granules is difficult to achieve. The efficiency of the manual shaking movement depends not only on the skill and patience of the operator but also by the additional amount of air taken into the mixing chamber. Since the front cap is permeable to blood, there is a limit to the vehemence of the shaking movement, unless a further closure is provided.

Another serious disadvantage of the known apparatus resides in the fact that air is introduced into the mixture due to the shaking movement, which air impairs the quality of the finished bone filling mass and which can be removed only in part and only with considerable effort.

DE-3,701,190-A discloses a device for sucking in or discharging liquid or pasty masses including bone cement, in which a piston is sealed with respect to a cylinder by means of a lip seal surrounding the piston so that air trapped in the mass within the cylinder can be withdrawn by a vacuum source connected to the cylinder behind the piston.

SUMMARY OF THE INVENTION

It is an object of the present invention to provide a granules syringe which permits an effective impregnation of the granules.

It is another object of the invention to devise a syringe which ensures an efficient removal of air from the final mixture of granules and liquid.

It is a further object of the invention to provide a granules syringe that is simple to handle.

These and other objects are met by a syringe for impregnating granules with a liquid and for dispensing the impregnated granules, which comprises a generally cylindrical barrel forming a chamber for receiving the granules and having a dispensing front end, a removable cover defining a front limitation of the chamber, the cover being permeable to the liquid, an air-permeable plug movably disposed within the barrel and defining a rear limitation of the chamber, a piston reciprocally disposed within the barrel at the rear side of the plug remote from the chamber, and valve means disposed at the rear side of the plug, the valve means being closed when the piston is retracted away from the front end of the barrel, and being open when the piston is advanced towards the front end.

In the granules syringe according to the invention, the impregnating liquid is sucked through the granules by retracting the piston without increasing the volume of the chamber containing the granules. This will ensure an intensive impregnation without requiring shaking. At the same time, any air initially contained in the granules is removed by being drawn through the porous plug.

BRIEF DESCRIPTION OF THE DRAWING

The drawing is a sectional view of a granules syringe taken along the axis thereof.

DETAILED DESCRIPTION OF A PREFERRED EMBODIMENT

The granules syringe shown in the drawing comprises a tubular cylindrical barrel 10 preferably made of glass or a transparent synthetic material and having a length of, e.g., 120 mm and an outer diameter of, e.g., 10 mm. Adjacent a discharge opening 11, the barrel 10 forms a chamber rearwardly confined by a plug 12 for receiving granules 13 which may have a mean particle diameter of 1 mm. The rear end of the barrel 10 remote from the discharge opening 11 is open and provided with an outer grip flange 14.

A piston rod 15 is inserted into the barrel 10 through the rear opening thereof and is provided at its rear end with a grip disc 16 and at its front end with a piston head 17. The piston rod 15 is suitably shaped so that air to be removed can excape rewardly. A star-shaped cross-section is well suited for this purpose.

In the initial condition shown in the drawing, the piston head 17 abuts the rear side of the plug 12. The piston rod 15 is preferably designed so that the front surface of the plug 12 is flush with the front discharge opening 11 of the barrel 10 when the piston rod 15 is advanced to its maximum extent with the disc 16 abutting the flange 14.

The piston head 17 is conically tapered and has its smallest rear end connected to the central axial portion of the piston rod 15 by means of an axial peg 18. The peg 18 passes through an O-ring 19 the outer edge of which sealingly engages the cylindrical interior wall of the barrel 10. When the piston rod 15 is retracted, the inner hole of the O-ring 19 sealingly engages the conical rear surface of the piston head 17. When the piston is advanced, the O-ring 19 disengages from the piston head 17, so that an air passage is formed through the inner hole of the O-ring 19.

The plug 12 consists of a porous material, such as sintered polyethylene, having a pore size of, e.g., 150 μm. The porositiy is selected such that the plug 12 is permeable to air but prevents the granules 13 from escaping. Further, the porosity can be selected such that it cannot be readily penetrated by the impregnating liquid, e.g. blood.

In the initial condition of the syringe shown in the drawing, a cap 20 is fitted or screwed onto the discharge end of the barrel 10, with a disc 21 of porous material closing the discharge opening 11. The material of the disc 21 may be sintered polyethylene similar to that of the plug 12. The pore size is selected such that the disc 21 is permeable to the liquid used for impregnating the granules 13, but is impervious to the granules 13 themselves.

The granules syringe described above is supplied by the manufacturer in the condition shown in the drawing, including a filling of granules 13. In use, the syringe with the cap 20 fitted onto it is immersed into the liquid, which is drawn through the porous disc 21 within the cap 20 and the granules 13 by retracting the piston rod 15 including the piston head 17 and the O-ring 19. Because the barrel 10 is transparent, the operator can observe the liquid as it penetrates the granules 13. When the liquid reaches the plug 12, the withdrawing action of the piston is terminated. In this condition, the granules are completely saturated.

The piston is subsequently returned into its initial position. During this movement, air which has been sucked from the granules and passed through the plug 12 will now escape rearwardly through the valve opening formed by the inner hole of the O-ring 19. For subsequently dispensing the impregnated granules, the cap 20 with the porous disc 21 is removed and the plug 12 is then advanced by means of the piston head 17.

The plug 12 is so dimensioned that it is retained within the cylindrical barrel 10 with sufficient strength to avoid backward movement by the vacuum formed to take in the liquid when the piston is retracted. An alternative or additional measure for preventing such a rearward movement of the plug 12 may be provided by an abutment formed on the inner cylindrical wall of the barrel 10 behind the plug 12.

The valve-type seal described above, which is integrated in the piston and formed by the O-ring 19, the piston head 17 and the piston rod 15, constitutes only one embodiment. A seal which is closed when the piston is retracted and opened when the piston is advanced, may be alternatively achieved by a correspondingly shaped sealing lip of the piston head 17. The same action may be further achieved by a valve disposed behind the plug 12 in the wall of the barrel 10.

Similarly, the star-shaped cross-section of the piston rod 15 is only one embodiment for achieving an air passage through the length of the piston rod 15.

The granules syringe described above is primarily intended for use in preparing and dispensing granules of bone cement impregnated with the respective patient's blood for filling cavities in the patient's bone. The invention is not, however, restricted to such a use.

What is claimed is:

1. A syringe for impregnating granules with a liquid and for dispensing the impregnated granules, comprising
   (a) a generally cylindrical barrel forming a chamber for receiving the granules and having a dispensing front end,
   (b) a removable cover defining a front limitation of said chamber, said cover being permeable to said liquid,
   (c) an air-permeable plug movably disposed within said barrel and defining a rear limitation of said chamber,
   (d) a piston reciprocally disposed within said barrel at the rear side of said plug remote from said chamber, said piston being separate from said plug and retractable away from said plug when said granules are impregnated with the liquid, said piston contacting said plug and moving the same during the dispensing operation, and
   (e) valve means disposed at the rear side of said plug, said valve means being closed when said piston is retracted away from said front end of said barrel, and being open when said piston is advanced toward said front end.

2. The syringe of claim 1, wherein said valve means includes seal means on said piston engaging the inner peripheral wall of said barrel, said valve means being integral with said seal means.

3. The syringe of claim 1, wherein said piston has a passage extending throughout its length and being open to the atmosphere at the rear end of the piston, and a head portion formed at the front end of said piston and constituting a seat, said valve means including seal means being formed by an O-ring which engages said seat when said piston is retracted, and disengages from said seat when the piston is advanced to establish a communication between the rear side of said plug and said passage.

4. The syringe of claim 1, wherein said barrel is made of transparent material.

5. The syringe of claim 1, wherein said cover is held in position by a cap adapted to be fixed to the front end of said barrel.

* * * * *